United States Patent [19]
Fried et al.

[11] Patent Number: 5,608,106
[45] Date of Patent: Mar. 4, 1997

[54] PREPARATION OF ALKOXYALKANOIC ACIDS

[75] Inventors: Herbert E. Fried; David M. Singleton; Raul A. Pabon, Jr., all of Houston, Tex.

[73] Assignee: Shell Oil Company, Houston, Tex.

[21] Appl. No.: 439,499

[22] Filed: May 11, 1995

[51] Int. Cl.$^6$ ................................................. C07C 51/235
[52] U.S. Cl. ........................ 562/538; 562/537; 562/540; 562/421
[58] Field of Search .................................. 562/421, 538, 562/537, 540

[56] References Cited

U.S. PATENT DOCUMENTS

| | | | |
|---|---|---|---|
| 3,998,924 | 12/1976 | Jones et al. | 423/7 |
| 4,348,509 | 9/1982 | Sanders et al. | 562/538 |
| 4,620,033 | 10/1986 | Isshiki et al. | 562/519 |
| 5,136,101 | 8/1992 | Fried | 568/402 |
| 5,136,102 | 8/1992 | Fried | 568/402 |
| 5,136,103 | 8/1992 | Fried | 568/402 |
| 5,155,278 | 10/1992 | Fried | 568/471 |
| 5,155,279 | 10/1992 | Fried | 568/471 |
| 5,155,280 | 10/1992 | Fried | 568/471 |
| 5,162,579 | 11/1992 | Fried | 562/537 |
| 5,166,422 | 11/1992 | Fried | 562/537 |
| 5,166,423 | 11/1992 | Fried | 562/537 |
| 5,175,359 | 12/1992 | Fried | 562/537 |
| 5,175,360 | 12/1992 | Fried | 562/538 |
| 5,179,218 | 1/1993 | Fried | 554/134 |
| 5,239,116 | 8/1993 | Fried | 562/537 |
| 5,250,727 | 10/1993 | Fried | 562/540 |
| 5,380,930 | 1/1995 | Fried | 562/537 |
| 5,387,712 | 2/1995 | Fried | 562/420 |
| 5,391,822 | 2/1995 | Fried | 562/538 |

FOREIGN PATENT DOCUMENTS 50-96516  7/1975  Japan .

OTHER PUBLICATIONS

Miyazawa et al., "Oxidation of Benzyl Alcohol with Iron(III) Using Polymers Containing Nitroxyl Radical Structure as a Mediator," J. Polym. Sci., Polym. Chem. Ed., 23 (9), 1985, pp. 2487–2494.

Miyazawa et al., "Oxidation of Benzyl Alcohol with Copper(II) Mediated by a Polymeric Oxoaminium Salt," J. Mol. Catal., 49(1), 1988, 131–134. (Abstract only).

Ganem et al., "Biological Spin Labels as Organic Reagents. Oxidation of Alcohols to Carbonyl Compounds Using Nitroxyls," J. Org. Chem., 40(13), 1975, pp. 1998–2000. (Abstract only).

Miyazawa et al., "Oxidation of Benzyl Alcohol by Iron(III) Mediated by Nitroxyl Radical." J. Mol. Catal., 31(2), 1985, pp. 217–220.

Annelli et al., "Fast and Selective Oxidation of Primary Alcohols to Aldehydes or to Carboxylic Acids and of Secondary Alcohols to Ketones Mediated by Oxoammonium Salts under Two–Phase Conditions," J. Org. Chem., 52(12), 1987, pp. 2559–2562.

Inokuchi et al., "A Selective and Efficient Method for Alcohol Oxidations Mediated by N–Oxoammonium Salts in Combination with Sodium Bromite," J. Org. Chem., 1990, 55 pp. 462–466.

Organic Synthesis, vol. 69, p. 212 (1990).

Semmelhack et al., "Oxidation of Alcohols to Aldehydes with Oxygen and Cupric Ion, Mediated by Nitrosonium Ion," J. Am. Chem. Soc., 1984, 106, 3374–3376.

Yamaguchi et al., "Application of Redox System Based on Nitroxides to Organic Synthesis," Pure & Applied Chemistry, vol. 62(2), 1990, 217–222.

E. S. Kagan et al., "Chemistry of Hindered Amines from the Piperidine Series", Synthesis, 1984, pp. 895–916.

R. M. Dupeyre et al., "Nitroxides. XIX. Norpseudopelletierine–N–oxyl, a New, Stable, Unhindered Free Radical," JACS, 88 (13), 1966, pp. 3180–3181.

E. G. Rozantsev et al., "Synthesis and Reaction of Stable Nitroxyl Radicals I. Synthesis" Synthesis, Apr. 1971, pp. 190–202.

E. G. Rozantsev et al., "Synthesis and Reaction of Stable Nitroxyl Radicals II. Reactions," Synthesis, Apr. 1971, pp. 401–414.

*Primary Examiner*—Gary Geist
*Assistant Examiner*—Rosalynd A. Williams
*Attorney, Agent, or Firm*—Pamela J. McCollough

[57] ABSTRACT

A process for preparing an alkoxyalkanoic acid by reacting the corresponding alkoxyalkanol with a resin-supported stable free radical nitroxide in the presence of a $NO_x$-generating compound and, optionally, an oxidant and/or a solvent at a temperature in the range of from about 0° C. to about 100° C. and thereafter separating out the alkoxyalkanoic acid.

33 Claims, No Drawings

PREPARATION OF ALKOXYALKANOIC ACIDS

FIELD OF THE INVENTION

This invention relates to a process for the preparation of alkoxyalkanoic acids by the oxidation of the corresponding alkoxyalkanols in the presence of a resin-supported stable free radical nitroxide and a $NO_x$-generating compound and, optionally, an oxidant and/or a solvent.

BACKGROUND OF THE INVENTION

Alkoxyalkanoic acids are useful as anionic surfactants or emulsifying agents. These acids, being composed of only the elements C, H and O, do not pose the environmental problems that other detergents containing heteroatoms such as N, S, and P pose. The alkoxyalkanoic acids can be prepared in a two-step process of first reacting an alkanol with an alkoxylate and a suitable alkoxylation catalyst and thereafter converting the resultant alkoxyalkanol to the alkoxyalkanoic acid.

It is also known to convert alkoxyalkanols such as methyl carbitol to the corresponding carboxylic acids by oxidizing them with nitric acid. However, relatively large amounts of nitric acid are required and not all of the nitric acid can be separated by distillation. In addition, cleavage of the ether linkages occurs to a large degree during this process.

Japanese Patent No. 50-96516, issued July 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.–270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, Vol. 52 (12), pp. 2559–2562; *Pure and Applied Chemistry*, Vol. 62(2), 1990, pp. 217–222; *Journal of Organic Chemistry*, Vol. 55, 1990, pp. 462–466. The primary products produced in these processes are aldehydes and the stoichiometrically consumed oxidant is hypochlorite.

It is generally more difficult to oxidize alkoxyalkanols than alkanols as it is difficult to oxidize alkoxyalkanols without splitting the molecular chain at the ether linkage and thereby produce a large proportion of undesired by-product. It would therefore be advantageous to produce alkoxyalkanoic acids in high yields and with high selectivities without producing large amounts of other products such as aldehydes, esters, and alkanoic acids. It would also be advantageous to have a supported nitroxide to make separation of the product easier and to enable the supported nitroxide to be isolated and reused.

It has been found that alkoxyalkanoic acids having high selectivities can be produced without forming highly corrosive, difficult to separate, side-products by using catalytic amounts of a resin-supported stable free radical nitroxide, a $NO_x$-generating compound and, optionally, an oxidant and/or a solvent.

SUMMARY OF THE INVENTION

This invention relates to a process for preparing an alkoxyalkanoic acid by reacting the corresponding alkoxyalkanol with a resin-supported stable free radical nitroxide in the presence of a $NO_x$-generating compound at a temperature in the range of from about 0° C. to about 100° C. and thereafter separating out the alkoxyalkanoic acid.

In particular, this invention relates to a process for the preparation of an alkoxyalkanoic acid of the formula

wherein R is a primary alkyl, secondary alkyl, tertiary alkyl, aromatic or an alkyl aromatic group having from 1 to about 1000 carbon atoms, R' is hydrogen, alkyl, aryl or mixtures thereof (on the individual molecule) and n is an integer of from 1 to about 1000 which comprises reacting the corresponding alkoxyalkanol with a resin-supported stable free radical nitroxide having the formula:

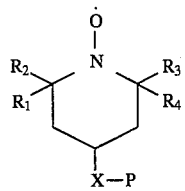

wherein each of $R_1$, $R_2$, $R_3$, and $R_4$ is an alkyl, aryl or substituted alkyl group having 1 to about 15 carbon atoms, X is selected from the group consisting of

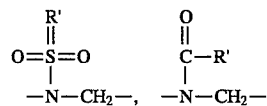

wherein R' is alkyl, aryl, or amido,

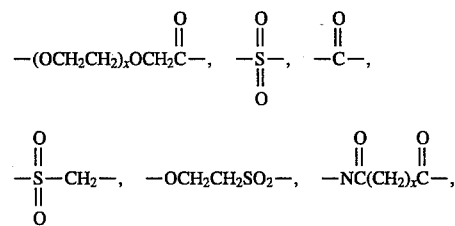

—O—$(CR''_2)_x$—$CH_2$ where R" is alkyl or hydrogen, and P is a polystyrene, in the presence of a $NO_x$-generating compound and, optionally, an oxidant at a temperature in the range of from about 0° C. to about 100° C. and thereafter separating out the alkoxyalkanoic acid.

DESCRIPTION OF THE PREFERRED EMBODIMENTS

The present process converts alkoxyalkanols of the formula

wherein R is a primary alkyl, secondary alkyl, tertiary alkyl, aromatic or an alkyl aromatic group having preferably 1 to about 1000; more preferably about 11 to about 18 carbon atoms, R' is hydrogen, alkyl, aryl or mixtures thereof (on the individual molecule) and n represents the average number of oxyalkylene groups and is an integer of from 1 to about 1000, preferably from about 2 to about 9, to the corresponding alkoxyalkanoic acids of the formula:

by contacting the alkoxyalkanol with a resin-supported stable free radical nitroxide in the presence of a $NO_x$-generating compound and, optionally, an oxidant and/or a solvent at a temperature in the range of from about 0° C. to about 100° C. and thereafter separating out the alkoxyalkanoic acid. The alkyl group, R, in the above formula I can be substituted with any substituent which does not interfere with the oxidation of the hydroxy group. Such substituents include —OR", —$CH_3$, —COOH, $CONH_2$ and COOR" wherein R" is an alkyl or aryl group.

The process of the instant invention is particularly suited to ethoxylated, or propoxylated alcohols with alkyl chains (R) of about 8 to about 20, preferably of about 11 to about 18 carbon atoms. The R' groups on an individual molecule can be hydrogen, alkyl, aryl or mixtures thereof. For example, straight ethoxylated, straight propoxylated and mixed ethoxylated-propoxylated detergent alcohols are available. The number of such alkoxylate groups, ($CH_2CHR'O$), typically ranges from about 1 to about 1000. Commercially, detergent range ethoxylated alcohols are available with an average of 3, 7, 9 and 12 ethoxylate units per molecule. Others can be readily prepared. In a preferred embodiment, the starting alkoxyalkanol is an ethoxylated alcohol which has had the unreacted alcohols and lower ethoxylates topped off in order to give an ethoxylated alcohol having about 3 to about 4 ethylene oxide units per molecule.

The term "stable free radical nitroxide" as used herein shall mean a free radical nitroxide or nitroxyl that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in-situ.

The stable free radical nitroxides, as used in the present process, are precursors to catalysts, i.e., oxoammonium salts, active for the oxidation of alkoxyalkanols to the corresponding acids. These catalysts are generated in situ by the oxidation of a stable free radical nitroxide to an oxoammonium salt. The stable free radical nitroxide can be obtained by the oxidation of secondary amines or hydroxylamines.

The stable free radical nitroxides which are suitable for use in the instant invention are those which are bound to or supported on a resin P with a linkage of X and have the formula:

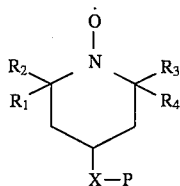 (III)

wherein each of $R_1$, $R_2$, $R_3$ and $R_4$ is an alkyl, aryl or substituted alkyl group and no hydrogen is bound to the remaining valences of the carbon atoms bound to the nitrogen. In the above formula III, X is selected from the group consisting of

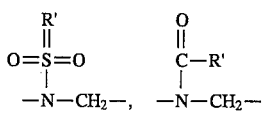

wherein R' is alkyl, aryl, or amido,

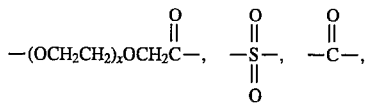

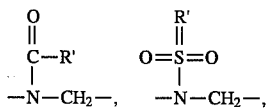

—O—$(CR"_2)_x$—$CH_2$ wherein R" is alkyl or hydrogen, with

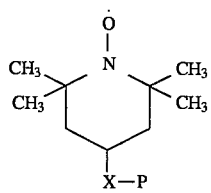

and —O—$(CR"_2)_x$—$CH_2$ being preferred and P is a polystyrene. As used herein the term "alkyl" is meant to include cycloalkyl. The alkyl (or heteroatom substituted) groups $R_1$, $R_2$, $R_3$ and $R_4$ may be the same or different, and preferably contain 1 to 15 carbon atoms. Preferably, $R_1$, $R_2$, $R_3$ and $R_4$ are methyl, ethyl, or propyl groups. In addition to hydrogen, the heteroatom substituents may include, halogen, oxygen, nitrogen and the like, as long as such substituents do not interfere with the oxidation reaction.

In a preferred embodiment, the resin-supported stable free radical nitroxide is a resin-supported 2,2,6,6-tetramethylpiperidin-1-oxyl, i.e. a resin-supported 2,2,6,6-tetramethyl-1-piperidinyloxy, having the formula:

(IV)

The stable free radical nitroxide is supported on a resin, P, with a linkage, X. Particularly suitable resins include those which are 1–2% cross-linked with divinylbenzene and which contain 1–4 milliequivalents per gram (meg/g) of benzylic chloride. Resins such as Merrifield's resin, which is comprised of chloromethylated polystyrene are particularly preferred. The resin supported nitroxides are typically prepared by contacting an amine-containing stable free radical nitroxide with chloromethylated polystyrene in the presence of a solvent such as, for example, dimethylformamide, at temperatures in the range of from about 20° C. to about 135° C. The resulting product is then acetylated with acetic anhydride in order to provide a suitable resin-supported nitroxide which is suitable for use in the present invention and which gives a linkage which is stable under the acidic oxidative reaction conditions.

Suitable linkages, X, are those which, as set forth above, are stable under oxidative and acidic reaction conditions. Suitable linkages include the group consisting of

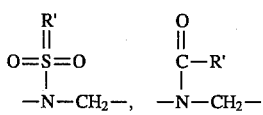

wherein R' is alkyl, aryl, or amido

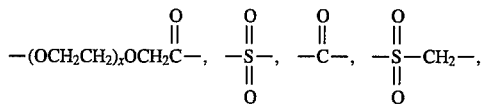

—OCH$_2$CH$_2$SO$_2$—,

—O—(CR''$_2$)$_x$—CH$_2$ wherein R'' is alkyl or hydrogen. In a preferred embodiment, the linkage is selected from

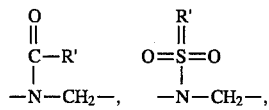

and —O—(CR''$_2$)$_x$—CH$_2$.

The NO$_x$-generating compound in the present process is typically selected from the group consisting of an alkali metal nitrosodisulfonate, nitric acid and mixtures thereof, with nitric acid being preferred. However, any compound which serves to generate NO$_x$ during the course of the reaction and which does not interfere with the reaction would be suitable. While not wishing to be bound by any particular theory, it is believed that nitrogen oxides (NO$_x$) are generated in the reaction and are required to generate the active catalytic species.

The alkali metal nitrosodisulfonate suitable for use as a NO$_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added. Generally, the amount of alkali metal nitrosodisulfonate used is in the range of from about 1 mole percent to about 1000 mole percent, basis the moles of starting alkoxyalkanol.

As used herein, the term "nitric acid" refers to nitric acid, fuming nitric acid, nitrous acid, nitrogen dioxide or dinitrogen tetraoxide generated by contacting alkali metal nitrite with mineral acid. Nitric acid can also be generated by contacting alkali metal nitrate with mineral acid. The nitric acid suitable for use in the present invention typically has a concentration in the range of from about 25 percent to about 100 percent, preferably about 70 percent. Generally, an amount of nitric acid in the range of from about 1 mole percent to about 1000 mole percent, basis the moles of starting alkoxyalkanol is utilized. The nitric acid is typically added to the reaction mixture after all of the other reactants have been added.

The process of the present invention may be carried out in the presence or absence of an oxidant. In a preferred embodiment, the process is carried out in the presence of an oxidant. However, when the process is carried out in the presence of an excess of the NO$_x$-generating compound, an oxidant is not needed. The oxidants suitable for use in the instant invention are those compounds which are capable, in the presence of nitric acid, of oxidizing the stable free radical nitroxide to the oxoammonium salt. Suitable oxidants include oxygen-containing gases such as pure oxygen and oxygen in air. Whereas pure oxygen is preferred to accomplish the desired conversion, the oxygen can also be diluted with an inert gas such as nitrogen, helium, argon, or other similar gas. While air can be used as the oxidant, the reaction rate is slower. For purposes of increasing the reaction rate, higher O$_2$ pressures such as, for example, 1000 psig can be utilized. In a preferred embodiment, pure oxygen is used as the oxidant and it is bubbled into the reaction solution.

The reaction in the instant invention can be carried out in the presence or absence of a solvent. When the reaction is carried out in the presence of a solvent, the solvent is generally a solvent in which the alkoxyalkanol is readily soluble. Solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of acetonitrile, tertiary alcohols such as tertiary butyl alcohol, dichloromethane, chlorobenzene, chloroform, carbon tetrachloride, dichloroethylene, dimethoxyethane, acetic acid, alkyl ethoxycarboxylate and mixtures thereof. In a preferred embodiment, the solvent is selected from the group consisting of acetonitrile, dichloromethane and mixtures thereof. The ratio of solvent to starting alkoxyalkanol utilized in the process is typically in the range of from about 20:1 to about 0.5:1 and preferably in the range of from about 5:1 to about 1:1.

The amounts and concentrations of the reactants utilized in the process of the instant invention can vary within wide ranges. The amount of stable free radical nitroxide is typically in the range of from about 0.1 mole percent to about 500 mole percent, preferably from about 1 mole percent to about 20 mole percent, basis the number of moles starting alkoxyalkanol. Generally, the amount of NO$_x$-generating compound used is in the range of from about 1 mole percent to about 1000 mole percent, basis the number of moles of alkoxyalkanol.

The process of the present invention is typically conducted under mild conditions, with good results being obtained using a temperature in the range of from about 0° C. to about 100° C., preferably about 20° C. to about 70° C., and most preferably, about 40° C. to about 60° C. When an alkali metal nitrodisulfonate is utilized as the NO$_x$-generating compound, a temperature of from about 0° C. to about 60° C. is preferred, and a temperature in the range of from about 30° C. to about 40° C. is particularly preferred. Reaction pressures are not critical although higher pressures may result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique such as for example, a fluidized bed or a flow reactor, to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.016 moles of alkoxyalkanol, and 3 grams of the resin-supported nitroxide, may be added to the reaction vessel, followed by the addition of 0.011 moles of nitric acid and 25 milliliters of solvent. The reaction vessel may then be heated to reaction temperature and sparged with oxygen at ambient pressure. Following the reaction, the product may be separated from the supported catalyst by filtration. The reaction product can be purified by a number of conventional means such as high temperature water washing or extraction.

Depending upon process conditions and the nitroxide used, the selectivity to alkoxyalkanoic acids obtained by this invention can be greater than about 95%. The products produced by the instant process can be used as emulsifying agents or in a variety of detergent applications. For example, light duty dishwashing liquids, shampoos and heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

Illustrative Embodiments

In the following examples, the starting alkoxyalkanol was a NEODOL® Ethoxylate 23-3T alcohol which was prepared by ethoxylating a mixture of $C_{12}$ and $C_{13}$ substantially straight chain alcohols ($C_{12}:C_{13}$ 40:60) to an ethoxylated alcohol having about 3 ethylene oxide units per molecule and then topping off the unreacted alcohols and lower ethoxylates so that the final product contains less than about 5 percent unreacted alcohol.

The resin-supported nitroxide in the following examples was prepared by reacting 1.2 equivalents of 4-amino-2,2,6,6-tetramethylpiperidin-1-oxyl and 2 equivalents of triethylamine with a 1% cross-linked chloromethylated styrene/divinylbenzene copolymer containing 1 milliequivalent per gram (meq/g) of active chloride in the presence of dimethylformamide. After filtration and rinsing with dimethylformamide, the material was treated with acetic anhydride.

EXAMPLE 1

6 Grams of the starting alkoxyalkanol, 3 grams of the resin-supported nitroxide, 25 milliliters of dichloromethane and 1 gram of 70 percent nitric acid were charged to a 100 milliliter round bottomed flask. Oxygen was bubbled through this stirred mixture at ambient pressure. The reaction was held at reflux over a 3-hour period. The liquid phase was then removed from the solid supported nitroxide by filtration. The results are presented in Table I.

EXAMPLE 2

6 Grams of the starting alkoxyalkanol, 25 milliliters of dichloromethane, 1 gram of 70 percent nitric acid, and the resin-supported nitroxide recovered from Example 1 above were charged to a 100 milliliter round bottomed flask. Oxygen was then bubbled through the reaction vessel at ambient pressure. The reaction was held at reflux over a 3-hour period. The results are presented in Table I.

EXAMPLE 3

12 Grams of the starting alkoxyalkanol, 6 grams of the resin-supported nitroxide, 25 milliliters of 1,2-dimethoxyethane, and 1 gram of 70 percent nitric acid were charged to a 100 milliliter glass vessel. Oxygen was then bubbled through the reaction vessel. The reaction temperature was held at 35° C. over a 4-hour period. The results are presented in Table I.

Comparative Example A

Comparative Example A was carried out in a manner similar to Example 1 except that no resin-supported nitroxide was used. The results are presented in Table I.

Comparative Example B

Comparative Example B was carried out in a manner similar to Example 1 except that no nitric acid was used. The results are presented in Table I.

As can be seen in Table I, both the resin-supported stable free radical nitroxide and nitric acid are necessary for the oxidation of the alkoxyalkanol to proceed. Example 2 shows that the resin-supported nitroxide can be recycled following previous use in an oxidative reaction.

TABLE I

Oxidation of Alkoxyalkanols to Alkoxyalkanoic Acids

| | % Conversion | % Selectivity to Acids | % Selectivity to Esters |
| --- | --- | --- | --- |
| Example 1 | 98 | 97 | 3 |
| Example 2 | 98 | 96 | 4 |
| Example 3 | 95 | 99 | 1 |
| Comparative Example A | <2 | 0 | 0 |
| Comparative Example B | 0 | 0 | 0 |

What is claimed is:

1. A process for preparing an alkoxyalkanoic acid by reacting the corresponding alkoxyalkanol with a resin-supported stable free radical nitroxide in the presence of a $NO_x$-generating compound at a temperature in the range of from about 0° C. to about 100° C. and thereafter separating out the alkoxyalkanoic acid.

2. The process of claim 1 wherein said process is carried out in the presence of an oxidant.

3. The process of claim 1 wherein the resin support is a chloromethylated styrene/divinylbenzene copolymer.

4. The process of claim 1 wherein said $NO_x$-generating compound is selected from the group consisting of nitric acid, an alkali metal nitrosodisulfonate and mixtures thereof.

5. The process of claim 4 wherein said $NO_x$-generating compound is nitric acid.

6. The process of claim 5 wherein said nitric acid is selected from the group consisting of fuming nitric acid, nitrous acid generated by contacting an alkali metal nitrite with mineral acid, nitric acid generated by contacting an alkali metal nitrate with mineral acid, nitrogen dioxide, and mixtures thereof.

7. The process of claim 5 wherein said nitric acid has a concentration in the range of from about 25 percent to about 100 percent.

8. The process of claim 5 wherein the amount of nitric acid is in the range of from about 1 mole percent to about 1000 mole percent, basis the number of moles alkoxyalkanol.

9. The process of claim 4 wherein said $NO_x$-generating compound is an alkali metal nitrosodisulfonate.

10. The process of claim 9 wherein the amount of alkali metal nitrosodisulfonate is in the range of from about 1 mole percent to about 1000 mole percent, basis the number of moles of alkoxyalkanol.

11. The process of claim 9 wherein said alkali metal nitrosodisulfonate is potassium nitrosodisulfonate.

12. The process of claim 1 wherein said process is carried out in the presence of a solvent.

13. The process of claim 12 wherein said solvent is selected from the group consisting of acetonitrile, tertiary alcohols such as tertiary butyl alcohol, dichloromethane, chlorobenzene, chloroform, carbon tetrachloride, dichloroethylene, dimethoxyethane, acetic acid, alkyl ethoxycarboxylate and mixtures thereof.

14. A process for the preparation of an alkoxyalkanoic acid of the formula

wherein R is a primary alkyl, secondary alkyl, tertiary alkyl, aromatic or an alkyl aromatic group having from 1 to about 1000 carbon atoms, R' is hydrogen or methyl or mixtures thereof (on the individual molecule) and n is an integer of from 1 to about 1000, which comprises reacting the corresponding alkoxyalkanol with a resin-supported stable free radical nitroxide having the formula:

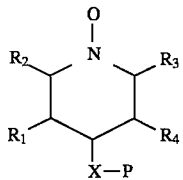

wherein (a) each of $R_1$, $R_2$, $R_3$, and $R_4$ is an alkyl, aryl or substituted alkyl group having 1 to about 15 carbon atoms, (b) X is selected from the group consisting of

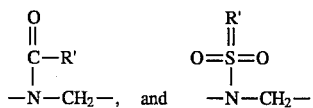

wherein R' is alkyl aryl or amido, and P is a polystyrene, in the presence of a $NO_x$-generating compound at a temperature in the range of from about 0° C. to about 100° C.

15. The process of claim 1 wherein P is a chloromethylated polystyrene.

16. The process of claim 14 wherein said $NO_x$-generating compound is selected from the group consisting of nitric acid, an alkali metal nitrosodisulfonate and mixtures thereof.

17. The process of claim 16 wherein said $NO_x$-generating compound is nitric acid.

18. The process of claim 16 wherein said nitric acid is selected from the group consisting of fuming nitric acid, nitrous acid generated by contacting an alkali metal nitrite with mineral acid, nitric acid generated by contacting an alkali metal nitrate with mineral acid, nitrogen dioxide, and mixtures thereof.

19. The process of claim 16 wherein said nitric acid has a concentration in the range of from about 25 percent to about 100 percent.

20. The process of claim 16 wherein the amount of nitric acid is in the range of from about 1 mole percent to about 1000 mole percent, basis the number of moles alkoxyalkanol.

21. The process of claim 16 wherein said $NO_x$-generating compound is an alkali metal nitrosodisulfonate.

22. The process of claim 20 wherein the amount of alkali metal nitrosodisulfonate is in the range of from about 1 mole percent to about 1000 mole percent, basis the number of moles of alkoxyalkanol.

23. The process of claim 20 wherein said alkali metal nitrosodisulfonate is potassium nitrosodisulfonate.

24. The process of claim 14 wherein said process is carried out in the presence of a solvent.

25. The process of claim 23 wherein said solvent is selected from the group consisting of acetonitrile, tertiary alcohols such as tertiary butyl alcohol, dichloromethane, chlorobenzene, chloroform, carbon tetrachloride, dichloroethylene, dimethoxyethane, acetic acid, alkyl ethoxycarboxylate and mixtures thereof.

26. The process of claim 14 wherein said alkoxyalkanol is contacted with said resin-supported stable free radical nitroxide, followed by the addition thereto of said $NO_x$-generating compound and said oxidant.

27. The process of claim 25 wherein the amount of resin-supported stable free radical nitroxide is in the range of from about 0.1 mole percent to about 500 mole percent, basis the number of moles of alkoxyalkanol.

28. The process of claim 26 wherein the amount of stable free radical nitroxide is in the range of from about 1 mole percent to about 20 mole percent, basis the number of moles of alkoxyalkanol.

29. The process of claim 25 wherein the amount of $NO_x$-generating compound is in the range of from about 1 mole percent to about 1000 mole percent, basis the number of moles of alkoxyalkanol.

30. The process of claim 14 wherein said process is carried out in the presence of an oxidant.

31. The process of claim 29 wherein said oxidant is an oxygen-containing gas.

32. The process of claim 30 wherein said oxygen-containing gas is selected from the group consisting of pure oxygen and air.

33. The process of claim 14 wherein said process is carried out at a temperature in the range of from about 20° C. to about 70° C. and at atmospheric pressure.

* * * * *